United States Patent [19]

Garzia et al.

[11] 4,273,931

[45] Jun. 16, 1981

[54] REDUCTION OF ALKYL ESTERS OF CARBONIC-CARBOXYLIC ANHYDRIDES TO ALCOHOLS

[75] Inventors: Aldo Garzia, Lodi; Giorgio Vittadini, Milan; Andrea Bottazzi, Lodi; Domenico Pelagalli, Lodi; Costantino Coccoli, Lodi, all of Italy

[73] Assignee: Istituto Chemioterapico Italiano, S.p.A., Milan, Italy

[21] Appl. No.: 105,537

[22] Filed: Dec. 20, 1979

[51] Int. Cl.$^3$ .............................................. C07C 33/20
[52] U.S. Cl. ................................... 546/344; 548/342; 548/343; 546/326; 260/545 R; 568/814; 568/884
[58] Field of Search ....................... 546/344; 548/342; 568/814, 884

[56] References Cited

PUBLICATIONS

Ishizumi et al., Chem. Pharm. Bull. 16(3), 492–497 (1968).
Seki et al., Chem. Pharm. Bull., 20(2), pp. 361–367 (1972).

*Primary Examiner*—Henry R. Jiles
*Assistant Examiner*—Bernard Dentz
*Attorney, Agent, or Firm*—Bernard & Brown

[57] ABSTRACT

There is disclosed the reduction of alkyl esters of carbonic-carboxylic acid anhydrides at elevated temperature and pressure in the presence of platinum group metal catalysts, especially palladium on activated carbon, to make alcohols. Novel alkyl esters of carbonic-carboxylic acid anhydrides are disclosed, and can be used to make the corresponding alcohols, e.g., substituted benzyl alcohols. The alcohols can be converted to the corresponding halo, e.g., chloro, compounds. The substituted benzyl halides can be reacted with di(lower alkoxy)propionitriles, and the resulting 5-benzyl pyrimidines such as trimethoprim, 2,4-diamino-5-(3,4,5-trimethoxybenzyl)-pyrimidine, which is a known anti-bacterial agent, are especially useful in combination with sulfa drugs such as sulfamethoxazole. Other alcohols that can be made in accordance with the invention include 2,6-pyridine dimethanol which can be used to make pyridinol carbamate, an anti-inflammatory agent and an anti-arteriosclerotic agent and 1-aceto-4-hydroxymethyl-5-methyl imidazole, which can be converted into cimetidine.

8 Claims; No Drawings

REDUCTION OF ALKYL ESTERS OF CARBONIC-CARBOXYLIC ANHYDRIDES TO ALCOHOLS

This invention relates to the manufacture of alcohols and to carbonic-carboxylic acid anhydride intermediates useful in the manufacture of alcohols by a reduction process. The invention particularly concerns alcohols of relatively complex structure compared with simple alcohols such as ethanol and methanol. The invention further relates to the use of derivatives of certain alcohols in preparing compounds that can be converted to products having desirable properties, e.g., anti-bacterial agents.

In some of its aspects, the invention is directed to the manufacture of arzyl, i.e., aryl—$CH_2$—, alcohols such as benzyl alcohols, especially substituted benzyl alcohols, for instance, alkoxy benzyl alcohols. The substituted benzyl alcohols can be used to produce compounds having anti-bacterial activity, for example, 2,4-diamino-5-benzyl pyrimidines such as trimethoprim, which is 2,4-diamino-5-(3,4,5-trimethoxybenzyl)-pyrimidine, a known anti-bacterial agent, that are especially useful in combination with sulfa drugs such as sulfamethoxazole.

The 2,4-diamino-5-benzyl pyrimidines are generally prepaed by multi-step procedures in which an aromatic aldehyde, e.g., an alkoxy-substituted benzaldehyde, is used as a reactant, see, for example, U.S. Pat. Nos. 3,049,544 and 3,341,541. These reactants are quite expensive to manufacture and, accordingly, other routes to the desired pyrimidines have been sought.

The present invention in one aspect is concerned with a process for making alcohols, especially aromatic group-containing alcohols such as benzyl alcohols. The aromatic group of the alcohols can have one or more substituents as in the case of the alkoxy-substituted benzyl alcohols. Also, by the present invention it has been found that the alcohols can be employed in the manufacture of other intermediates which in turn are useful in making 2,4-diamino-5-benzyl pyrimidines.

According to one aspect of the present invention, high yields of alcohols are obtained by reduction of alkyl esters of carbonic-carboxylic acid anhydrides at elevated temperature and elevated pressure under the influence of a sufficient amount of a platinum group metal reduction catalyst. Typically, the yields of alcohol obtained can be at least about 90 mole % of theoretical or even about 95 to 100%, in reasonable reaction periods. Suitable reaction temperatures are at least about 40° C., preferably at least about 50° C., and no particular reason has been found for using temperatures above about 120° C. The preferred reaction temperatures have been found to be about 50° and 100° C. The pressure employed during the reaction is elevated and can generally be at least about 5 atmospheres, preferably at least about 10 or 15 atmospheres. The molecular hydrogen present in the reduction reaction system can be added as such, preferably in relatively pure form, although mixed gases containing hydrogen can be used. The hydrogen or mixed gases can be employed to pressure the reaction vessel, and preferably hydrogen is present in excess of the stoichiometric amount.

The surface of the reaction vessel exposed to the reduction reaction of the invention should be composed of a material that does not unduly adversely affect or contaminate the reaction mixture with, for instance, metal ions or corrosion products. The material of construction is preferably essentially inert to the reactants, the reaction and the catalyst and, thus, does not poison or otherwise distract from the desired activity of the catalyst to a material extent. Suitable reaction vessel surfaces can be non-metallic materials such as glass, ceramics, glass-ceramics and the like. At least some metals may exhibit undesirable effects in these respects. The reaction may be conducted in the presence or absence of a solvent for the reactants and/or the products.

I am aware of the article by Seki, Koga and Yamada, Chem. Phar. Bull., 20 (2), 361–367 (1972) reporting the reaction of derivatives of alcohols or carboxylic acids to obtain products containing predominantly aldehydes. The authors refer to a number of prior reaction systems in this respect and their disadvantages. The article also points to previous work of the authors concerning the preparation in high yields of beta-amino alcohols and their N-acylated derivates by reduction of the corresponding alpha-amino acid esters or their N-acylated derivatives with sodium borohydride. The paper is mainly concerned with the manufacture of N-acylated, alpha-amino aldehydes from the corresponding N-acylated, alpha-amino acids and their derivatives, e.g., mixed carbonic-carboxylic acid anhydrides prepared by reaction of N-acylated, alpha-amino acids and their derivatives, e.g., mixed carbonic-carboxylic acid anhydrides prepared by reaction of N-acylated, alpha-amino acids and ethylchloroformate.

The Seki, Koga and Yamada article refers to prior work in which mixed carbonic-carboxylic acid anhydrides made from carboxylic acids and ethyl chloroformate were reduced with sodium borohydride to their corresponding alcohols in fair yields. The authors' work was concerned with conducting this type of reaction in the presence of a catalyst having palladium supported on a charcoal carrier, and ways in which the amounts of product aldehyde and alcohol varied under certain reaction conditions or environments. In most cases, the product contained considerably more aldehyde than alcohol, but when a base, i.e., triethylamine, was present and yields were greater than about 50% total aldehyde and alcohol, the latter component predominated. Even in such case, however, the yield of alcohol apparently leveled out at about 75% when the reaction was conducted at 3° to 5° C. which the authors concluded were the most appropriate temperatures to employ.

Many of the alkyl esters of carbonic-carboxylic acid anhydrides employed as reactants in making alcohols according to the invention have the formula:

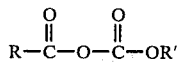

in which R is an organic radical which does not unduly interfere with the conversion of these materials to alcohols. The R' group represents the alkyl group in the alkyl ester of the carbonic-carboxylic acid anhydride designation and R' may be lower alkyl. Most conveniently, the R' group will have up to about 4 carbon atoms with ethyl being preferred. When the carboxylic acid contains a plurality of carboxylic groups, more than one of the latter may be converted to an alkyl carbonic-carboxylic acid anhydride structure. Thus in the case of dicarboxylic acids the alkyl ester of the carbonic-carboxylic acid anhydride may have the formula:

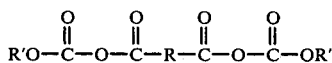

in which R is the divalent form of the same group or radical as described above. Such compounds may be depicted by the formula:

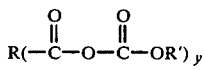

where y is 1 or more, e.g. up to about 3 or 4, but more often 1 or 2, preferably 1, and R is the y-valent form of the group.

The R substituent in the alkyl esters of carbonic-carboxylic acid anhydrides used to make alcohols according to this invention is organic and is generally composed to a major extent of carbon and hydrogen. Thus R may be a hydrocarbyl group which may contain other elements such as nitrogen and oxygen and be saturated or unsaturated. The R-substituent may be cyclic or acyclic or both, and thus may be aliphatic, including cycloaliphatic, aromatic, mixed aromatic-aliphatic, or heterocyclic, for instance, have nitrogen or oxygen in an otherwise carbocyclic ring structure. The R group may contain any desired number of carbon atoms, and often it may have up to about 20 carbon atoms or somewhat more. In many reactants of interest the number of carbon atoms in the R group may be up to about 10 or 12. The reduction reaction of the invention may be of most interest in making alcohols having a structure that is more complex than the simple alcohols such as methanol and ethanol which can be made by less involved procedures. Thus, the R substituent will frequently have at least about 4 or 6 carbon atoms. For example the R substituent may be, or contain, one or more groups such as phenyl, alkylphenyl, pyridyl, alkoxy, aminoalkyl, dialkylamino, alkoxyphenyl, chlorophenyl, N-acylaminoalkyl, imidazyl, alkyl imidazyl and the like.

In the alcohol products that can be used to make 2,4-diamino-5-arzyl pyrimidines, the R group of the alkyl ester of the carbonic-carboxylic acid anhydride reactant is aryl, e.g., phenyl, and may contain none or 1 to 3 groups on the aromatic ring, preferably two or three. Such groups may be hydrocarbyl, that is, composed to a major extent of carbon and hydrogen, although other elements, e.g., oxygen, may be present. The substituent groups on the aryl ring may thus be alkyl such as lower alkyl, and are preferably alkoxy, e.g., lower alkoxy, especially methoxy.

The alkyl ester of a carbonic-carboxylic acid anhydride reactants of the present invention can be made by reaction of the corresponding carboxylic acid and alkylchloroformate in a solvent such as tetrahydrofuran. This reaction is described by Ishizumi, Koga and Yamada in *Chem. Pharm. Bull.* (Tokyo), 16, 492 (1968). However, many of the reactants that can be used to make alcohols in accordance with this invention are considered to be new compounds having the formula

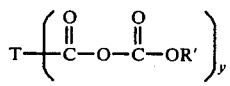

wherein T is, for example, $R_x^2Ar$, or Y defined below, in their monovalent or plural valent forms. Thus, y is the same as defined above. Such compounds include, for example, the following:

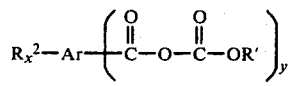

wherein Ar is aryl, especially phenyl, R' is as described above, $R^2$ is a substituent group, e.g., halogen such as chloro, fluoro or bromo, or a hydrocarbyl group such as alkyl or alkoxy, e.g., lower alkyl or lower alkoxy of say 1 to about 4 carbon atoms, especially methyl or methoxy, and x is 0 to 3, generally 1 to 3, preferably 2 to 3, or even 3 and y is as defined above. The aryl radical may contain other groups in addition to, or in place of, the designated $R^2$ groups, and Ar is generally hydrocarbyl. Preferably, $R^2$ is methoxy and R' is ethyl.

Other alkyl esters of carbonic-carboxylic acid anhydrides that are believed to be new include those of the formula:

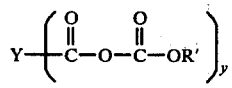

in which R' and y have the same definitions as above, and in which Y indicates a nitrogen-containing hydrocarbyl ring of say 4 to 6 carbon atoms such as pyridyl or imidazyl, which ring may be substituted or unsubstituted and saturated or unsaturated.

The catalysts that may be employed in the reduction reaction of the present invention contain a minor amount of platinum group metal distended or supported on a solid carrier. The platinum group metal component may include one or more of the members of that group such as palladium, platinum and rhodium, with a palladium being preferred. The amount of platinum group metal in the catalyst will often be at least about 0.05 weight % of the total weight of the catalyst. Generally, this amount need not exceed about 10 to 15%, and since these metals are quite expensive, the smallest suitable amount will often be employed, e.g., at least about 0.1 to 1%. The platinum group metals are generally in a dispersed form on the support.

The solid support or carrier of catalyst can be of various compositions. Carbon supports are preferred although other materials may be used, e.g., one or more refractory oxides such as silica, alumina, aluminosilicates and the like. Porous supports are preferred and thus the total surface area of the catalyst including its surface pores, may often be at least about 25 square meters per gram, preferably at least about 50 square meters per gram. Among the preferred supports are activated carbons having, for example, surface areas of at least about 100 square meters per gram.

The alcohols made in accordance with the present invention can be converted by known procedures to the corresponding halogen derivatives, i.e., compounds in which the hydroxy group of the alcohol positioned on the carbon atoms that is adjacent to the R group of the alkyl carbonic-carboxylic acid anhydride, e.g., $R(CH_2OH)_y$ or more particularly $T(CH_2OH)_y$, is converted to a halogen group such as fluoro, chloro or bromo, especially chloro. The products would have the formula R(CH$_2$Z)$_y$ and among these compounds are those having the structure:

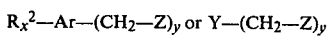

R$_x^2$—Ar—(CH$_2$—Z)$_y$ or Y—(CH$_2$—Z)$_y$ wherein Ar, R$^2$, x, y and Y have the same designations as indicated above with respect to the alkyl carbonic-carboxylic acid anhydrides, and Z is a halo group, e.g., fluoro, chloro or bromo.

Other alcohols that can be made in accordance with the invention includes pyridine 2,6-dimethanol as represented by the equations:

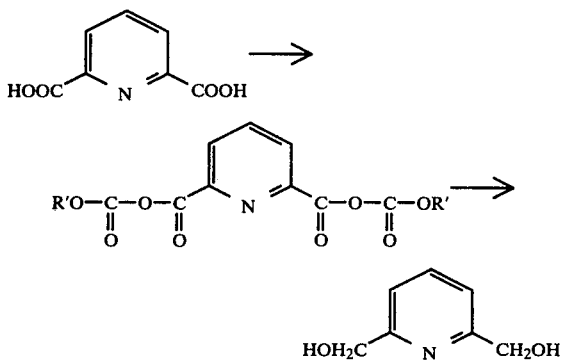

and 4-hydroxymethyl-5-methyl imidazole per the equations:

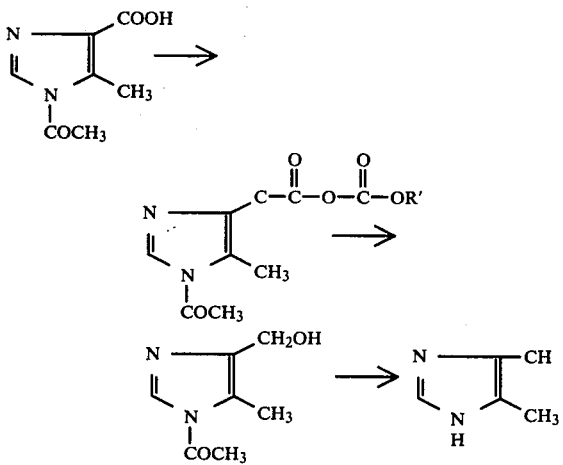

Pyridine 2,6-dimethanol is useful in making pyridinol carbamate [also known as 2,6-pyridinedimethanol bis (N-methylcarbamate)], which has utility as an anti-inflammatory agent and as an anti-arterioschloerotic agent. 1-aceto-4-hydroxymethyl-5-methyl imidazole is useful as an intermediate in making cimetidine which is useful in the treatment of gastric ulcers.

The RCH$_2$Z compounds are especially useful in making intermediates for conversion in the case of the R$_x^2$—Ar—CH$_2$—Z compounds to 2,4-diamino-5-arzyl pyrimidines, through a reaction which is also believed to be novel. These arzyl compounds thus contain the structure:

R$_x^2$—Ar—CH$_2$—.

The arzyl group is preferably R$_x^2$-benzyl. The hydroxy group of the above alcohols may be converted to a halo group by known procedures.

It is thus a further aspect of the present invention that the

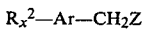

R$_x^2$—Ar—CH$_2$Z

Compounds can be converted in high yields to the corresponding 2,4-diamino-5-arzyl pyrimidines through reaction with dialkoxy nitriles of the formula:

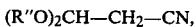

(R″O)$_2$CH—CH$_2$—CN, in which R″ is alkyl, e.g., lower alkyl of up to about 4 carbon atoms, especially methyl. The resulting compounds have the formula:

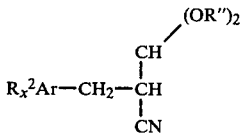

The reaction can proceed at ambient, reduced or somewhat elevated temperatures to say up to about 50° C., and various pressures may be employed. The reaction also yields the corresponding hydrohalide, HZ, and may be conducted in the presence or absence of a solvent, such as an aromatic solvent, e.g., toluene. The reaction can be catalyzed by the presence of a basic catalyst such as sodamide. The product compounds can be converted to 2,4-diamino-5-arzyl pyrimidines by reaction with guanidine as described, for instance in U.S. Pat. Nos. 3,049,544 and 3,341,541 and the examples below.

The various process parameters for the conversion of 3,4,5-trimethoxybenzoic acid (hereinafter referred to as TMB acid) to 3,4,5-trimethoxybenzyl alcohol (hereinafter referred to as TMB alcohol) are of interest since, for instance, this alcohol can be oxidized to the corresponding aldehyde. In this synthesis, the mixed anhydride of TMB acid is prepared by reacting the TMB acid in a reaction medium with an alkyl haloformate, e.g. ethyl chloroformate, in the presence of a tertiary amine such as triethylamine. The initial amount of TMB acid in the reaction medium may be equimolar relative to the alkyl haloformate and to the amine, although a slight excess of the acid (e.g. about 1–2%) may be preferred to avoid the presence of unsalified amine which may inhibit the catalyst used in the subsequent hydrogenation step. The preparation of the mixed anhydride from the TMB acid is suitably conducted in a reaction medium such as toluene or the like which is substantially free from sulfur-containing compounds and trace amounts of metals. Generally, it has been found that industrial grade reaction media are satisfactory for the purposes of the present invention.

During the course of the addition of tertiary amine and alkyl haloformate to the reaction medium containing the TMB acid, the temperature should be maintained at about 5° C. or less, since an elevated temperature such as about 20° C. or more tends to inhibit the formation of the anhydride. Thereafter, however, during the formation of the mixed anhydride, ambient temperature is generally satisfactory. The reaction may be allowed to proceed for about 1–3 hours, preferably about two hours, with continual agitation of the medium. Once the preparation of the mixed anhydride is completed, the formed amine crystals can be removed from the medium by filtering. The yield of the mixed anhydride from the TMB acid will generally approach about 100%.

The formed solution of the mixed anhydride may then be immediately subjected to further chemical reactions in accordance with the present invention or, alternatively, may be safely stored for further processing at a later date. It has been found that the mixed anhydride solution can be stored from about three days at a temperature of up to about 70° C. and still provide yields in the subsequent catalytic hydrogenation step which are only slightly less than if the solution be hydrogenated immediately.

Once the mixed TMB anhydride has been prepared, it can be subjected to catalytic hydrogenation in accordance with the present invention to produce TMB alcohol. In the catalytic hydrogenation, the mixed anhydride in the same toluene reaction medium and having catalyst added thereto can be introduced into a pressure vessel maintained at an elevated temperature, preferably about 65°–75° C., and having a hydrogen-containing atmosphere maintained at an elevated pressure, e.g. about 15 to 20 or so atmospheres measured at room temperature. The catalytic metal utilized is preferably palladium, e.g. 10% palladium supported on carbon. The hydrogenation is allowed to proceed for a suitable time, e.g. about 3 to 7 hours, with vigorous agitation so as to maintain the catalyst in suspension in the reaction medium. It has been found that the time period necessary for complete hydrogenation of the mixed anhydride to TMB alcohol is directly proportional to the efficiency of agitation of the reaction medium.

Upon completion of the hydrogenation, the catalyst is separated from the reaction medium by means such as filtration. The formed TMB alcohol may then be separated from the reaction medium by conventional techniques. The yield of TMB alcohol from the use of this method relative to the amount of initial TMB acid may vary according to the effect of the various reaction parameters but is generally in the range of about 90–97%.

The formed TMB alcohol may be directly reacted in the medium to produce other derivatives such as 3,4,5-trimethoxybenzaldehyde by methods such as oxidation with manganese dioxide or the like at elevated temperatures of about 70°–90° C. under vigorous agitation. In the oxidation reaction of TMB alcohol utilizing manganese dioxide, the molar ratio of the dioxide to the TMB alcohol is preferably at least about 4:1 since lower ratios such as 3:1 or 2:1 tend to produce lower yields of the aldehyde, even when the time of reaction is lengthened or when the reaction water is removed azeotropically. Preferably the manganese dioxide utilized in the oxidation reaction is activated prior to introduction into the reaction medium by means such as heating.

It is believed that most, if not all, of the procedures and reaction conditions used in the conversion of TMB acid to TMB alcohol set forth above are indicative of procedures and reaction conditions which may be used in the conversion of various carboxylic acid compounds to their respective alcohols. Consequently, those knowledgeable in the art will be able to readily adapt the method of the present invention to transform a wide variety of carboxylic acid compounds to their respective alcohols.

The present invention is represented in the following examples. The examples are given for the purpose of illustration only and should not limit the invention.

EXAMPLE I 3,4,5-trimethoxybenzyl alcohol was prepared from 3,4,5-trimethoxybenzoic acid and then subsequently oxidized to yield 3,4,5-trimethoxybenzylaldehyde. About 1,192 g. of 3,4,5-trimethoxybenzoic acid suspended in about 7 l. of toluene are made into a solution by the addition of a mixture of about 568 g of triethylamine and about 2.8 l. of toluene. To the solution thereby obtained, a mixture of about 619 g. of ethyl chloroformate and about 2 l. of toluene is slowly added, the temperature being maintained at around 5° C. After agitation for approximately 2 hours at ambient temperature, the formed triethylamine hydrochloride crystals are filtered from the reaction medium by being washed onto the filter with about 4 l. of toluene. A toluene solution of the mixed anhydride is thereby obtained, the solution being clear and colorless, generally stable at room temperature, and storable in polyethylene containers. The toluene solution consists of about 1.6 kg. of the mixed anhydride in about 16 l. of solution.

The mixed anhydride solution is then subjected to catalytic hydrogenation in a pressure vessel in the presence of about 112 g. 10% Pd on carbon catalyst and at a hydrogen pressure of about 18 atm, the initial pressure being measured at room temperature. During hydrogenation, the temperature is maintained at about 70° C. and the catalyst is kept in suspension by vigorous agitation. At the completion of the hydrogenation after about 4 hours, the catalyst is separated by filtration and is washed with a small amount of toluene which is then added to the reaction solution. The toluene solution obtained from the hydrogenation reaction contains 3,4,5-trimethoxybenzyl alcohol in the molar proportion of about 96% relative to the stoichiometric quantities of the starting material. Small amounts of the corresponding acid and aldehyde are also present.

The 3,4,5-trimethoxybenzyl (TMB) alcohol may be recovered from the solution by appropriate separation techniques or the alcohol may be reacted with hydrochloric acid to obtain 3,4,5-trimethoxybenzyl chloride or can be oxidized to 3,4,5-trimethoxybenzaldehyde by the following process. Prior to the commencement of the oxidation process, a quantity of manganese dioxide is activated by heating the dioxide in an oven for a period of about 36 hours. Then, to the above toluene solution of the TMB alcohol, about 1,880 g. of the activated manganese dioxide (molar ratio of about 4:1) is added and the reaction allowed to proceed for about 4 hours under vigorous agitation and at an elevated temperature of about 80° C.

At the completion of the reaction, the manganese dioxide is filtered off. The dioxide is washed thoroughly with about 6 l. of toluene and then with hot water, and is subsequently reheated in an oven so as to reactivated for further use.

Upon separation from the toluene solution, about 1 kg. of 3,4,5-trimethoxybenzaldehyde is realized from the latter oxidation reaction which is a stoichiometric yield of about 94–95% relative to the amount of 3,4,5-trimethoxybenzyl alcohol. The formed aldehyde has a melting point of about 74° C. and a titer of about 98%.

EXAMPLE II

Pyridine 2,5-dicarboxylic acid is reacted in a process similar to that utilized in the reaction of 3,4,5-trimethoxybenzoic acid set forth in the first two portions of the procedure of Example I so as to produce the corresponding mixed anhydride that is subjected to the catalytic hydrogatation to obtain pyridine 2,6-dimethanol.

EXAMPLE III 1-acetoimidazole-5-methyl-4-carboxylic acid is reacted in a process similar to that utilized in the reaction of 3,4,5-trimethoxybenzoic acid set forth in the first two portions of the procedure of Example I so as to produce the corresponding mixed anhydride that is subjected to the catalytic hydrogenation to obtain 1-aceto-4-hydroxymethyl-5-methyl-imidazole.

EXAMPLE IV

PREPARATION OF α-(3,4,5-TRIMETHOXYBENZYL)-β-DIMETHOXYPROPIONITRILE AND 2,4-DIAMINO-5-(3,4,5-TRIMETHOXYBENZYL)-PYRIMIDINE (1)

α-(3,4,5-trimethoxybenzyl)-β-dimethoxypropionitrile 11.5 g. of 1-cyano-2,2-dimethoxyethane are added to a suspension of 4 g. of sodamine in 100 ml. of anhydrous toluene. 21.6 g. of 3,4,5-trimethoxybenzyl chloride prepared as described in Example I are added to this mixture under agitation and cooling, the resulting mixture being then heated at 100° C. for 2 hours. The toluene solution is extracted after cooling with 200 cc. of water, and the organic phase is dried on anhydrous sodium sulfate. The toluene is evaporated at low pressure to obtain an oily residue which is distilled at low pressure. 21.7 g. of dense liquid (boiling point 158°–160° C./titer 95% (GLC)), which slowly crystallizes, are obtained after distillation. A sample of the crystallized methanol distillate melts at 69°–70° C.

(2) 2,4-diamino-5-(3,4,5-trimethoxybenzyl)-pyrimidine 48 g. of guanidine hydrochloride are added to a solution of 28 g. of sodium methylate of 500 m.l of anhydrous ethanol, and then 48 g. of distilled -(3,4,5-trimethoxybenzyl)-β-dimethopropionitrile (titer 95%) are added. The reaction mixture is subjected to reflux agitation for 48 hours. About 300 cc. of alcohol are removed by distillation, and the residue is cooled to −5° C. The residue is filtered and washed with a small amount of cold ethanol and then with water. 43 g. of 2,4-diamino-5-(3,4,5-trimethoxybenzyl)-pyrimidine (melting point 197°–190° C.) are obtained after drying. 39 g. of pure product (melting point 199°–200° C., yield 87% of the theoretical) are obtained after recrystallization from aqueous methanol.

It is claimed:

1. A method of making alcohols which comprises reducing an alkyl ester of a carbonic-carboxylic acid anhydride with hydrogen at temperatures of at least about 40° C. and elevated pressure, and in the presence of a catalyst comprising platinum group metal on a solid carrier.

2. The method of claim 1 in which the solid carrier of the catalyst comprises activated carbon.

3. The method of claim 1 or 2 in which the platinum group metal of the catalyst comprises palladium.

4. The method of claim 1 or 2 in which the pressure is at least about 10 atmospheres.

5. The method of claim 4 in which the platinum group metal of the catalyst comprises palladium.

6. A method of making alcohols which comprises reducing an alkyl ester of a carbonic-carboxylic acid anhydride of the formula:

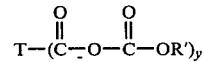

wherein $R'$ is lower alkyl, T is $R_x{}^2 Ar$ or Y, Ar is aryl, $R^2$ is a member selected from the group consisting of lower alkyl, lower alkoxy and halogen, x is 0 to 3, y is 1 to 3 and Y is a nitrogen-containing hydrocarbyl ring of 4 to 6 carbon atoms, with hydrogen at temperatures of at least about 40° C. and elevated pressure, and in the presence of a catalyst comprising platinum group metal on a solid carrier.

7. The method of claim 6 in which the catalyst comprises palladium on charcoal and the pressure of the reaction is at least about 10 atmospheres.

8. The method of claim 6 or 7 in which Ar is phenyl and $R^2$ is lower alkoxy.

* * * * *